(12) United States Patent
Donnigan et al.

(10) Patent No.: US 8,663,270 B2
(45) Date of Patent: Mar. 4, 2014

(54) JAW MOVEMENT MECHANISM AND METHOD FOR A SURGICAL TOOL

(75) Inventors: Stephen Donnigan, Highlands Ranch, CO (US); Eric Sugalski, Cambridge, MA (US); Erik Holverson, Naperville, IL (US); Randall Koplin, Sun Prairie, WI (US); Michael Gregor, Chicago, IL (US)

(73) Assignee: Conmed Corporation, Utica, NY (US)

( * ) Notice: Subject to any disclaimer, the term of this patent is extended or adjusted under 35 U.S.C. 154(b) by 150 days.

(21) Appl. No.: 12/842,327

(22) Filed: Jul. 23, 2010

(65) Prior Publication Data
US 2012/0022584 A1  Jan. 26, 2012

(51) Int. Cl.
*A61B 17/00* (2006.01)

(52) U.S. Cl.
USPC ........... 606/208; 606/205; 606/206; 606/207; 227/60; 81/418; 81/176.3; 30/211; 30/217; 30/242; 30/258

(58) Field of Classification Search
USPC ........ 606/1, 205–208, 210, 250–253; 227/60; 433/159; 294/99.2; 81/418, 176.3; 30/211, 217, 242, 258
See application file for complete search history.

(56) References Cited

U.S. PATENT DOCUMENTS

| | | |
|---|---|---|
| 1,470,914 A | 10/1923 | Day |
| 1,539,831 A | 6/1925 | Day |
| 3,149,015 A | 9/1964 | Lindsay |
| 3,895,636 A | 7/1975 | Schmidt |
| 3,981,308 A | 9/1976 | Schlein |
| 4,241,861 A | 12/1980 | Fleischer |
| 4,572,185 A | 2/1986 | Rich |
| 4,674,501 A | 6/1987 | Greenberg |
| 4,907,589 A | 3/1990 | Cosman |
| 4,919,152 A | 4/1990 | Ger |
| 5,002,051 A | 3/1991 | Dew et al. |
| 5,009,661 A | 4/1991 | Michelson |
| 5,116,332 A | 5/1992 | Lottick |
| 5,211,655 A | 5/1993 | Hasson |
| 5,222,973 A | 6/1993 | Sharpe et al. |
| 5,281,220 A | 1/1994 | Blake, III |
| 5,282,817 A | 2/1994 | Hoogeboom et al. |
| 5,286,255 A | 2/1994 | Weber |
| 5,307,976 A * | 5/1994 | Olson et al. ................. 227/175.3 |
| 5,314,424 A | 5/1994 | Nicholas |
| 5,318,589 A | 6/1994 | Lichtman |
| 5,334,198 A | 8/1994 | Hart et al. |
| 5,336,232 A | 8/1994 | Green et al. |
| 5,358,506 A * | 10/1994 | Green et al. ................. 606/151 |

(Continued)

FOREIGN PATENT DOCUMENTS

| | | |
|---|---|---|
| CH | 70697 A | 3/1916 |
| DE | 2627679 A | 1/1977 |

(Continued)

*Primary Examiner* — Katherine Dowe
*Assistant Examiner* — Sidharth Kapoor (57) ABSTRACT

A jaw movement mechanism for surgical tools has improved mechanical efficiency and other advantages. The jaw movement mechanism controls the orientation and position of a movable jaw relative to a fixed jaw through a range of movement of the movable jaw. The jaws maintain a parallel orientation throughout a portion of the range of movement of the movable jaw. The jaws maintain an angular relationship throughout a portion of the range of movement of the movable jaw.

10 Claims, 4 Drawing Sheets

(56) References Cited

U.S. PATENT DOCUMENTS

| | | | |
|---|---|---|---|
| 5,431,674 | A | 7/1995 | Basile et al. |
| 5,474,637 | A | 12/1995 | Soodak |
| 5,478,351 | A | 12/1995 | Meade et al. |
| 5,480,409 | A | 1/1996 | Riza |
| 5,486,189 | A | 1/1996 | Mudry et al. |
| 5,496,347 | A | 3/1996 | Hashiguchi et al. |
| 5,499,992 | A | 3/1996 | Meade et al. |
| 5,499,998 | A | 3/1996 | Meade |
| 5,522,830 | A | 6/1996 | Aranyi |
| 5,571,216 | A | 11/1996 | Anderson |
| 5,573,534 | A | 11/1996 | Stone |
| 5,609,601 | A | 3/1997 | Kolesa et al. |
| 5,611,813 | A | 3/1997 | Lichtman |
| 5,618,304 | A | 4/1997 | Hart et al. |
| 5,620,459 | A | 4/1997 | Lichtman |
| 5,637,111 | A * | 6/1997 | Sutcu et al. .................. 606/51 |
| 5,662,667 | A | 9/1997 | Knodel |
| 5,735,849 | A | 4/1998 | Baden et al. |
| 5,749,893 | A | 5/1998 | Vidal et al. |
| 5,752,973 | A | 5/1998 | Kieturakis |
| 5,776,130 | A | 7/1998 | Buysse et al. |
| 5,792,138 | A | 8/1998 | Shipp |
| 5,836,960 | A | 11/1998 | Kolesa et al. |
| 5,849,022 | A | 12/1998 | Sakashita et al. |
| 5,853,412 | A | 12/1998 | Mayenberger |
| 5,968,074 | A | 10/1999 | Prestel |
| 6,001,096 | A | 12/1999 | Bissinger et al. |
| 6,039,733 | A | 3/2000 | Buysse et al. |
| 6,063,086 | A | 5/2000 | Benecke et al. |
| 6,099,550 | A | 8/2000 | Yoon |
| 6,179,834 | B1 | 1/2001 | Buysse et al. |
| 6,235,027 | B1 | 5/2001 | Herzon |
| 6,245,065 | B1 | 6/2001 | Panescu et al. |
| 6,270,508 | B1 | 8/2001 | Klieman et al. |
| 6,402,747 | B1 | 6/2002 | Lindemann et al. |
| 6,409,728 | B1 | 6/2002 | Ehr et al. |
| 6,458,130 | B1 | 10/2002 | Frazier et al. |
| 6,464,702 | B2 | 10/2002 | Schulze et al. |
| 6,511,480 | B1 | 1/2003 | Tetzlaff et al. |
| 6,514,252 | B2 | 2/2003 | Nezhat et al. |
| 6,517,536 | B2 | 2/2003 | Hooven et al. |
| 6,533,778 | B2 | 3/2003 | Herzon |
| 6,546,935 | B2 | 4/2003 | Hooven |
| 6,554,829 | B2 | 4/2003 | Schulze et al. |
| 6,582,451 | B1 | 6/2003 | Marucci et al. |
| 6,585,735 | B1 | 7/2003 | Frazier et al. |
| 6,623,482 | B2 | 9/2003 | Pendekanti et al. |
| 6,626,901 | B1 | 9/2003 | Treat et al. |
| 6,682,528 | B2 | 1/2004 | Frazier et al. |
| 6,695,840 | B2 | 2/2004 | Schulze |
| 6,716,232 | B1 | 4/2004 | Vidal et al. |
| 6,723,109 | B2 | 4/2004 | Solingen |
| 6,740,085 | B2 | 5/2004 | Hareyama et al. |
| D490,896 | S | 6/2004 | Bogazzi |
| 6,773,435 | B2 | 8/2004 | Schulze et al. |
| 6,860,880 | B2 | 3/2005 | Treat et al. |
| 6,905,497 | B2 | 6/2005 | Truckai et al. |
| 6,908,463 | B2 | 6/2005 | Treat et al. |
| 6,923,806 | B2 | 8/2005 | Hooven et al. |
| 6,984,233 | B2 | 1/2006 | Hooven |
| 6,994,709 | B2 | 2/2006 | Iida |
| 7,001,382 | B2 | 2/2006 | Gallo, Sr. |
| 7,006,874 | B2 | 2/2006 | Knowlton et al. |
| 7,063,699 | B2 | 6/2006 | Hess et al. |
| 7,083,618 | B2 | 8/2006 | Couture et al. |
| 7,090,673 | B2 | 8/2006 | Dycus et al. |
| 7,101,371 | B2 | 9/2006 | Dycus et al. |
| 7,101,372 | B2 | 9/2006 | Dycus et al. |
| 7,101,373 | B2 | 9/2006 | Dycus et al. |
| 7,108,694 | B2 | 9/2006 | Miura et al. |
| 7,115,123 | B2 | 10/2006 | Knowlton et al. |
| 7,118,570 | B2 | 10/2006 | Tetzlaff et al. |
| 7,118,587 | B2 | 10/2006 | Dycus et al. |
| 7,131,971 | B2 | 11/2006 | Dycus et al. |
| 7,137,980 | B2 | 11/2006 | Buysse et al. |
| 7,150,097 | B2 | 12/2006 | Sremcich et al. |
| 7,150,749 | B2 | 12/2006 | Dycus et al. |
| 7,156,846 | B2 | 1/2007 | Dycus et al. |
| 7,169,153 | B2 | 1/2007 | Keller |
| 7,182,775 | B2 | 2/2007 | de Guillebon et al. |
| 7,211,080 | B2 | 5/2007 | Treat et al. |
| 7,241,292 | B2 | 7/2007 | Hooven |
| 7,255,697 | B2 | 8/2007 | Dycus et al. |
| 7,288,098 | B2 | 10/2007 | Huitema et al. |
| 7,329,256 | B2 | 2/2008 | Johnson et al. |
| 7,329,257 | B2 | 2/2008 | Kanehira et al. |
| 2003/0065358 | A1 * | 4/2003 | Frecker et al. ................. 606/205 |
| 2003/0199870 | A1 | 10/2003 | Truckai et al. |
| 2004/0193199 | A1 | 9/2004 | Hashiguchi |
| 2005/0165429 | A1 | 7/2005 | Douglas et al. |
| 2005/0256522 | A1 | 11/2005 | Francischelli et al. |
| 2005/0256523 | A1 | 11/2005 | Chen et al. |
| 2005/0273085 | A1 | 12/2005 | Hinman et al. |
| 2006/0047278 | A1 | 3/2006 | Christian et al. |
| 2006/0129146 | A1 | 6/2006 | Dycus et al. |
| 2006/0206110 | A1 | 9/2006 | Knowlton et al. |
| 2006/0224158 | A1 | 10/2006 | Odom et al. |
| 2006/0271041 | A1 | 11/2006 | Eder et al. |
| 2006/0271042 | A1 | 11/2006 | Latterell et al. |
| 2007/0055231 | A1 | 3/2007 | Dycus et al. |
| 2007/0173813 | A1 | 7/2007 | Odom |
| 2007/0173814 | A1 | 7/2007 | Hixson et al. |
| 2007/0260238 | A1 | 11/2007 | Guerra |
| 2008/0004639 | A1 | 1/2008 | Huitema et al. |
| 2008/0009860 | A1 | 1/2008 | Odom |
| 2008/0015575 | A1 | 1/2008 | Odom et al. |
| 2008/0039836 | A1 | 2/2008 | Odom et al. |
| 2008/0187989 | A1 | 8/2008 | McGreevy et al. |
| 2008/0188844 | A1 | 8/2008 | McGreevy et al. |
| 2008/0188845 | A1 | 8/2008 | McGreevy et al. |
| 2009/0112254 | A1 * | 4/2009 | Yates ........................... 606/207 |

FOREIGN PATENT DOCUMENTS

| EP | 0503662 A1 | 9/1992 |
|---|---|---|
| JP | 8196540 A | 8/1996 |
| SU | 728848 A | 5/1980 |

\* cited by examiner

JAW MOVEMENT MECHANISM AND METHOD FOR A SURGICAL TOOL

CROSS REFERENCE TO RELATED APPLICATION

This invention is related to an invention described in U.S. patent application Ser. No. 12/842,399, titled Surgical Tool with Crossbar Lever, filed concurrently herewith and assigned to the assignee hereof. The subject matter of this related patent application is incorporated herein by this reference.

FIELD OF THE INVENTION

This invention relates to a surgical tool having jaws which grasp or otherwise manipulate tissue during a surgical procedure. More particularly, the invention relates to a surgical tool in which the jaws are positioned at one end of a long and narrow shaft assembly and a handle assembly operating mechanism is connected at the other end of the shaft to operate the jaws, thereby allowing the shaft assembly to be inserted through a cannula or endoscope when performing laparoscopic, endoscopic or other minimally invasive surgical procedures. Even more specifically, the present invention relates to a new and improved jaw movement mechanism which achieves greater tissue-gripping force and efficiency while moving the jaws in both angular or pivoted and parallel relationships during different parts of their relative movement.

BACKGROUND OF THE INVENTION

Minimally invasive laparoscopic surgery typically involves making a few small incisions through the outer muscular wall of the body, inserting cannulas through the incisions, adding carbon dioxide or argon gas to inflate the body wall away from the internal organs and thereby create a body cavity, inserting a miniature camera, a light and surgical tools through working channels of the cannulas into the body cavity, and performing the surgical procedure using the surgical tools with the aid of the camera while the gas maintains the inflated condition of the body cavity. Minimally invasive endoscopic surgery typically involves inserting an endoscope through an orifice of the body to gain access to an internal organ such as the lungs, stomach or intestines, and inserting a surgical tool through a working channel of the endoscope. In some circumstances another working channel of the endoscope houses a camera or other optical viewing device and light.

In general, these and other types of minimally invasive surgery require the surgical tool to have an operative device or capability at the end of a relatively long shaft assembly which fits through the working channel, with a handle assembly or other manipulating device connected at the opposite end of the shaft assembly so that the surgeon can manipulate the operative device which contacts the tissue. One common type of operative device is a pair of opposing jaws which are controlled by a jaw movement assembly. The jaws contact, grasp and manipulate tissue.

The jaws, jaw movement assembly and the shaft assembly of the surgical tool must be narrow enough in a transverse dimension to fit through the operating channel of the cannula or the endoscope. The two most common sizes of operating channels are slightly larger than 5 mm across and slightly larger than 10 mm across, thereby allowing a surgical tool having a 5 mm or 10 mm maximum transverse dimension to be inserted through those operating channels. The movement of the jaws is typically accomplished by relative reciprocating longitudinal movement between an outer tubular housing of the shaft assembly and an interior rod within the shaft assembly, and that longitudinal movement is transferred by the jaw movement mechanism into motion which opens the jaws laterally enough to accept and squeeze the tissue between the jaws. The handle assembly at the opposite end of the shaft assembly typically includes a handgrip with a lever which is squeezed to create the relative reciprocating longitudinal movement between the outer shaft housing and the interior shaft rod.

The narrowness of the shaft assembly and jaw movement mechanism imposes structural and functional limits on the amount of force which can be transmitted to the jaws. The jaw movement mechanism converts the relative reciprocating longitudinal movement of the shaft housing and the shaft rod into transverse movement of the jaws. The mechanical geometry involved in this conversion usually diminishes the force available from the jaws compared to the force available due to the relative movement of the shaft housing and shaft rod. Some of the mechanical force applied to the jaw movement mechanism is lost due to frictional resistance between moving parts of the jaw movement mechanism. The narrowness of the shaft assembly, jaw movement mechanism and jaws also limits the degree and extent of movement of the jaws. Because the jaws must not extend any wider than the operating channel when the jaws are closed, the jaw movement mechanism must establish a movement geometry which causes the jaws to open or separate sufficiently to grasp a desired amount of tissue, yet close to a position where the jaws are positioned very close to one another.

One advantageous type of jaw movement mechanism causes one or both of the jaws to separate from a closed position in a parallel manner until a certain degree of separation is achieved, and then moves one or both of the jaws in a pivotal manner similar to scissors to open the distal tip ends wider than the proximal ends. The completely open pivotal action allows more tissue to be located between the jaws and makes it easier for the surgeon to contact tissue which is to be grasped between the jaws. The closing parallel movement is advantageous in many surgical procedures to apply uniform pressure across the tissue which is grasped between the jaws.

Applying uniform pressure as a result of parallel closing jaw movement is particularly useful for those types of surgical tools which join, weld or fuse tissue together. In these types of instruments, heater elements or electrodes are attached to or incorporated in the jaws to allow the application of thermal energy to the tissue grasped by and compressed between the jaws. Fusion of the tissue pieces results from the simultaneous application of pressure and heat. The heat comes directly from the heater elements or is created by current flowing in the tissue between the electrodes on the jaws. Tissue fusion is typically performed on vessels to block the fluid or blood flow carried by the vessels. Achieving good tissue fusion is substantially enhanced if the vessel walls are compressed together with uniform pressure. Uniform pressure is obtained from the parallel closing movement of the jaws, and the uniform pressure is more likely to achieve an effective, leak-proof seal. Additionally, the parallel withdrawal of the jaws for limited range of motion after the tissue fusion has occurred is less likely to damage the seal which has been formed. The parallel withdrawal movement avoids a mechanical shearing action on the tissue which would occur if the jaws opened by a pivoting separation movement.

A common type of jaw movement mechanism which is capable of transferring longitudinal relative reciprocating motion into parallel movement of the jaws when closely approximated and into pivoting movement of the jaws when further separated involves two sets of pins and slots. Each of the two slots has a predetermined geometric and angular shape, and each of the two pins moves within its own slot. The slots may be formed in a distal end of the shaft housing, or in an attachment on the shaft housing, or in one or both of the jaws. The pins may likewise be attached to the distal end of the shaft housing, or to an attachment on the shaft housing, or in one or both of the jaws. The relative longitudinal reciprocating motion of the shaft housing and shaft rod moves the pins in relative position within the slots, and the geometry of the slots in relation to the position of the pins in those slots cause the jaws to move with a pivoting motion when the jaws are significantly separated and to move toward one another with parallel motion when the jaws become closer to one another. In some types of jaw movement mechanisms, only one pin and slot combination is used, coupled with some other form of mechanical movement-inducing device.

A drawback of the pin and slot type of jaw movement mechanism is that a significant amount of the force from relative longitudinal reciprocating movement of the shaft housing and the shaft rod is lost due to sliding frictional contact of the pins with the slots. The geometric orientation of the slots involves portions which are inclined with respect to one another, and the movement of the pin along the inclined portion of the slot generates substantial friction and reduces the amount of force available to move the jaws. This frictional sliding contact reduces the mechanical efficiency of the jaw movement mechanism. The amount of efficiency lost by the frictional engagement of the pins with the slots can reduce the amount of force available on the jaws to the point where the pressure is insufficient for tissue sealing.

SUMMARY OF THE INVENTION

The present invention substantially reduces the amount of frictional sliding contact between pins moving in slots of a jaw movement mechanism of a surgical tool of the type which opens and closes the jaws with parallel movement when the jaws are relatively close to one another and opens and closes the jaws with pivotal movement when the jaws are relatively farther away from one another. The present invention also enhances the mechanical force transferring capability and efficiency of the type of jaw movement mechanism which uses a pin in a slot to move a jaw member by reducing the amount of friction created by the pin moving in the slot. Furthermore, the present invention achieves more compression force by the jaws on the tissue in relation to the amount of force transferred through the relative longitudinal reciprocating movement of the shaft housing and the shaft rod.

In accordance with one aspect of the invention, a minimally invasive surgical tool has jaws for grasping tissue by relative transverse movement. The jaws are located at a distal end of a shaft assembly connected to a handle assembly. The handle assembly creates relative reciprocating movement transferred through relatively stationary and movable shaft members of the shaft assembly to a jaw movement mechanism. The jaw movement mechanism includes first and second pins respectively moving within first and second slots to convert the relative reciprocating movement of the shaft members into the relative transverse movement of the jaws. An improvement involves a pivot link pivotally connected between the relatively stationary shaft member and a movable one of the jaws to maintain a longitudinal position of the movable jaw during relative transverse movement independently of the pins contacting the slots.

Because the pivot link restrains the movable jaw against longitudinal movement, the energy losses due to frictional contact between the pins in the slots to maintain the longitudinal position of the relatively movable jaw is eliminated or substantially reduced, thereby reducing the amount of frictional sliding contact between pins moving in the slots and correspondingly increasing the amount of force available to move the jaws. The mechanical force transferring capability and efficiency is improved, and more compression force from the jaws on the tissue is available in relation to the amount of force generated at the handle assembly.

Another aspect of the invention, which achieves the same beneficial improvements, involves a method of constraining two jaws to move between a fully opened position wherein a straight working surface of each jaw extends at an angular orientation to the straight working surface of the other jaw at a relative great transverse separation distance of the jaws from one another and to move to a fully closed position where the working surfaces extend in a parallel orientation to one another at a relatively adjacent transverse distance from one another, in a minimally invasive surgical tool. In the surgical tool, the jaws are located at a distal end of a shaft assembly connected to a handle assembly which transfers relative reciprocating movement through relatively stationary and movable shaft members of the shaft assembly to a jaw movement mechanism. The jaw movement mechanism converts the relative reciprocating movement of the shaft members into the relative transverse movement of the jaws. The method comprises using first and second pins respectively moving within first and second slots in the jaw movement mechanism to convert the relative reciprocating movement of the shaft members into the relative transverse movement of the jaws. The method also comprises pivotally connecting a pivot link between the relatively stationary shaft member and a movable one of the jaws to maintain a longitudinal position of the movable jaw during relative transverse movement independently of the pins contacting the slots.

Additional features of both the apparatus and method of the present invention involve creating a fully opened position of the jaws where the straight working surfaces extend at an angular orientation to one another at a relative great transverse separation distance from one another and to create a fully closed position where the working surfaces extend in a parallel orientation to one another at a relatively adjacent transverse distance from one another; creating an intermediate position where the working surfaces extend in the parallel orientation to one another at a relatively greater transverse distance and at a relatively lesser transverse distance than the position of the working surfaces in the fully closed and fully opened positions, respectively; maintaining the parallel orientation of the working surfaces during relative transverse movement of the jaws between the fully closed and intermediate positions; farther separating the first and second pins in the first and second slots with movement of the jaw members from the intermediate position to the fully closed position; and using an interior rod as the relatively stationary shaft member, positioning the interior rod within a sleeve housing, and constraining the sleeve housing and the interior rod to prevent relative rotational movement while permitting relative longitudinal reciprocating movement.

A more complete appreciation of the present invention and its scope may be obtained from the accompanying drawings, which are briefly summarized below, from the following detailed description of a presently preferred embodiment of the invention, and from the appended claims.

DETAILED DESCRIPTION

Figure 1:
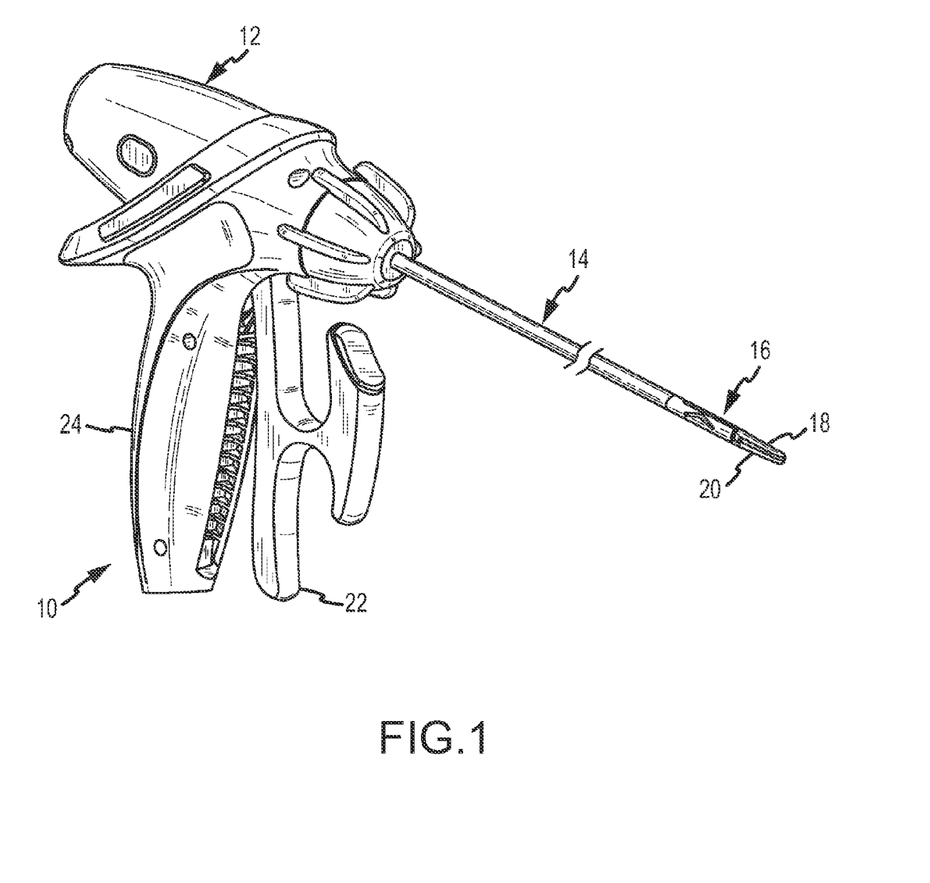
FIG. 1 is a perspective view of a surgical tool having a jaw movement mechanism which incorporates the present invention.

A surgical tool 10 which is useful in performing minimally invasive surgical procedures and which incorporates the present invention, is shown in FIG. 1. The surgical tool 10 includes a handle assembly 12, a shaft assembly 14 connected to the handle assembly, a jaw movement mechanism 16 located at a distal end of the shaft assembly 14, and jaws 18 and 20 connected to and moved by the jaw movement mechanism 16. The movement of the jaws 18 and 20 is shown in FIGS. 2-4.

The handle assembly 12 includes a movable lever 22 which pivots relative to a fixed handgrip 24, as shown in FIG. 1. The shaft assembly 14 includes longitudinally relatively movable shaft members in the form of a sleeve housing 26 (FIG. 5) within which an interior rod 28 (FIG. 5) is located. An internal mechanism (not shown) within the handle assembly 12 converts the relative pivoting movement of the lever 22 and the handgrip 24 into relative longitudinal reciprocating movement of the sleeve housing 26 and the interior rod 28. The relative longitudinal reciprocating motion of the sleeve housing 26 and the interior rod 28 is applied to the jaw movement mechanism 16, and the jaw movement mechanism 16 converts the longitudinal reciprocating movement into movement of the jaws 18 and 20 into and between an open pivoted position, an intermediate position and a closed position, respectively shown in FIGS. 2-4.

Each of the jaws 18 and 20 has a working surface 30 and 32, respectively, which contacts and compresses tissue 34. The working surfaces 30 and 32 of the jaws 18 and 20 are substantially straight or flat when viewed from the side, as shown in FIGS. 2-4 (and FIGS. 6-8). Discussion herein regarding the orientation of the jaws 18 and 20 refers to the orientation of the working surfaces 30 and 32 as viewed from the side of the jaws 18 and 20.

Figure 2:
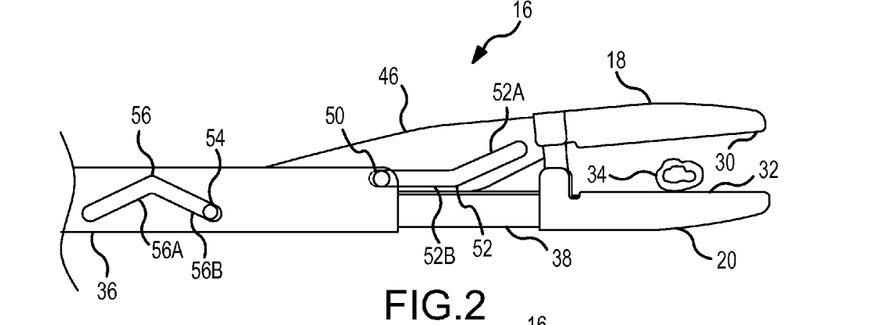
FIG. 2 is an enlarged elevation view of the jaw movement mechanism shown in FIG. 1, showing the jaws of the surgical tool in the fully opened, pivoted position.
Figure 3:
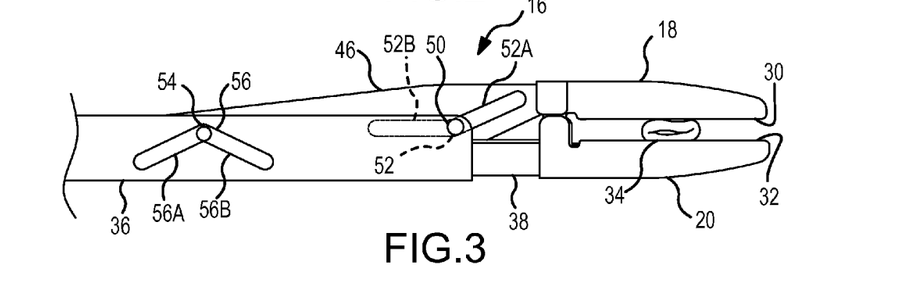
FIG. 3 is a view similar to FIG. 2 showing movement of the jaws by the jaw movement mechanism from the pivoted position shown in FIG. 2 to an intermediate position in which the jaws are parallel to and proximally spaced from one another.
Figure 4:
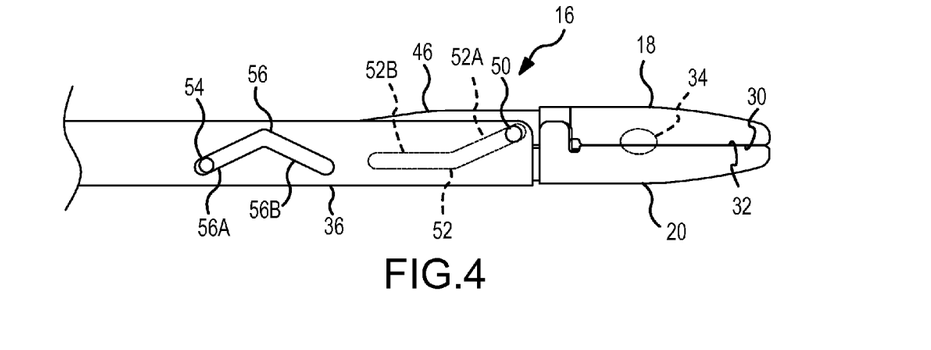
FIG. 4 is a view similar to FIGS. 2 and 3 showing movement of the jaws by the jaw movement mechanism from the intermediate position shown in FIG. 3 to a fully closed position in which the jaws are parallel to one another and contact one another.

The surfaces 30 and 32 assume an intersecting angular or pivoted orientation when the jaws 18 and 20 are in the fully open position shown in FIG. 2, and during movement from the fully open position to the intermediate position shown in FIG. 3. The angle between the surfaces 30 and 32 is the greatest when the jaws 18 and 20 are in the fully open position shown in FIG. 2. The wide angular separation of the working surfaces 30 and 32 in the fully opened position makes it easier to capture tissue 34 between the jaws.

The angular intersection of the pivoted orientation of the surfaces 30 and 32 diminishes to zero degrees to establish a parallel orientation as the jaws 18 and 20 move into the intermediate position shown in FIG. 3. In the intermediate position shown in FIG. 3, the surfaces 30 and 32 assume a parallel relationship with respect to one another, at a position where the working surfaces 30 and 32 are separated from one another. The tissue 34 between the working surfaces 30 and 32 is generally evenly distributed and slightly compressed between the working surfaces 30 and 32 at the intermediate position (FIG. 3), before a much greater degree of compression and force is applied to the tissue 34 when moving to the fully closed position (FIG. 4, shown without the tissue 34 between the jaws).

As the jaw movement mechanism 16 moves the jaws 18 and 20 from the intermediate position shown in FIG. 3 to the fully closed position shown in FIG. 4, the working surfaces 30 and 32 remain in a parallel relationship and orientation with respect to one another. The parallel orientation of the working surfaces 30 and 32 compresses the tissue evenly. In a tissue fusion surgical procedure, uniform compression of the tissue is important in achieving a good seal.

In the fully closed position, the distance between the working surfaces 30 and 32 diminishes to the point where the working surfaces 30 and 32 become very closely separated from one another as a result of substantially compressing the tissue 34 between the working surfaces. The degree of compression is substantial enough that only a very thin layer of tissue 34 exists between the working surfaces. The situation is illustrated in FIG. 4, where the degree of compression of the tissue between the surfaces 30 and 32 is so extensive that the tissue is not visible.

The degree of separation of the working surfaces 30 and 32 in the fully closed position is considerably less than the separation distance between the surfaces 30 and 32 when the jaws 18 and 20 are in the intermediate position (FIG. 3). The separation of the working surfaces 30 and 32 in the fully closed position may result only from mechanical distortion of the components due to the resistance created by compressing the tissue 34. Under circumstances of a lesser compression resistance from the tissue, or the absence of tissue between the working surfaces 30 and 32, the working surfaces 30 and 32 may contact one another.

More details concerning the jaw movement mechanism 16 and the jaws 18 and 20 and their movement are described below in conjunction with FIGS. 5-8, taken in connection with the earlier description in conjunction with FIGS. 1-4.

Figure 5:
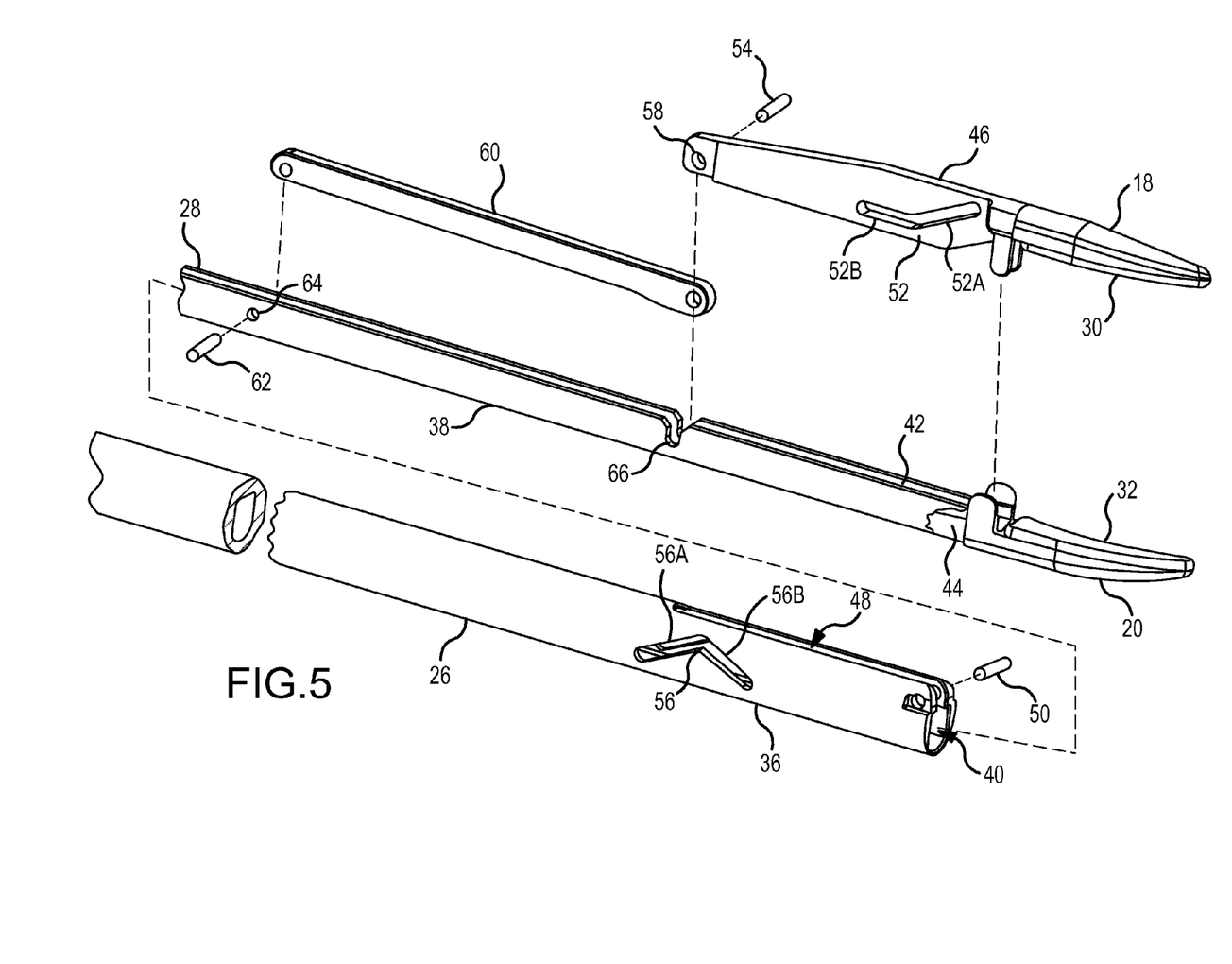
FIG. 5 is an exploded partial perspective view of the jaw movement mechanism, the jaws and distal ends of a shaft assembly of the surgical tool shown in FIGS. 1-5.

The jaw movement mechanism 16 includes a distal end portion 36 of the sleeve housing 26 and a distal end portion 38 of the interior rod 28. The sleeve housing 26 includes an interior 40 which receives the interior rod 28, as shown in FIG. 5. The interior 40 has a cross-sectional shape which conforms substantially with the exterior shape of the interior rod 28, thereby preventing the sleeve housing 26 and the interior rod 28 from rotating relative to one another. Sufficient clearance exists between the exterior of the interior rod 28 and the interior 40 of the sleeve housing 26 to permit the relative longitudinal reciprocating movement of the sleeve housing 26 and the interior rod 28.

The jaw 20 is rigidly attached to and extends from the distal end portion 38 of the interior rod 28. The interior rod 28 has a generally U-shaped cross-sectional configuration, and the U-shaped cross-sectional configuration defines an interior space 42 (FIG. 5) that extends along the length of the interior rod 28. The jaw 20 includes a rear extension portion 44 (FIG. 5) which is received within and rigidly connected to the interior space 42 of the interior rod 28, such as by welding or by brazing. Connected in this manner, the jaw 20 (hereinafter referred to as the fixed jaw 20) does not move relative to the interior rod 28.

The jaw 18 (hereinafter referred to as the movable jaw 18) is movably retained by the jaw movement mechanism 16. Movement of the movable jaw 18 causes its working surface 30 to move relative to the working surface 32 of the fixed jaw 20, thereby attaining the positions and movement shown and described herein (FIGS. 2-4 and 6-8). The movable jaw 18 includes a rear extension portion 46. A channel 48 is formed in the distal end portion 36 of the sleeve housing 26 in alignment with the rear extension portion 46 to accommodate and position the rear extension portion 46 of the movable jaw 18. During movement into the fully open and intermediate positions (FIGS. 2, 3, 7 and 8), the rear extension portion 46 moves laterally outward of the sleeve housing 26 through the channel 48.

The orientation of the movable jaw 18 relative to the fixed jaw 20 is defined by the movement of a forward pin 50 within and relative to a forward slot 52 and the simultaneous movement of a rear pin 54 within and relative to rear slots 56. The relative movement of the pins and slots occurs because of the reciprocating motion of the sleeve housing 26 and the interior rod 28. The forward pin 50 spans the channel 48 near the forwardmost end of the distal end portion 36 of the sleeve housing 26. The forward slot 52 is formed through the rear extension portion 46 of the movable jaw 18. With the forward pin 50 located in the forward slot 52, the rear extension portion 46 of the movable jaw 18 surrounding the forward pin 50 follows the path defined by the forward slot 52 during relative longitudinal reciprocating movement of the sleeve 26 and the interior rod 28.

The rear slots 56 are formed in the opposite sides of the distal end portion 36 of the sleeve housing 26 at transversely adjacent positions. The rear slots 56 share identical shapes as viewed from the sides of the sleeve housing 26. The rear pin 54 extends through a hole 58 formed in a rear end of the rear extension portion 46 of the movable jaw 18. The opposite ends of the rear pin 54 each fit within one of the rear slots 56. With the rear pin 54 located in the rear slots 56, the proximal end of the rear extension portion 46 of the movable jaw 18 follows the path defined by the rear slots 56 during relative longitudinal reciprocating movement of the sleeve housing 26 and the interior rod 28.

The rear pin 54 also pivotally connects a distal end of a pivot link 60 to the proximal end of the extension portion 46 of the movable jaw 18. A proximal end of the pivot link 60 is pivotally connected to the interior rod 28 by a pivot pin 62 located in a hole 64 at a position proximally separated from the location of the rear pin 54. The ends of the pivot pin 62 are located at the outer surface of the interior rod 28, and the interior 40 of the sleeve housing 26 maintains the pivot pin 62 in the hole 64. An indentation 66 is formed in the interior rod 28 to avoid interfering with the movement of the rear pin 54. The pivot link 60 is located within the interior space 42 of the interior rod 28.

The pivot link 60 retains the movable jaw 18 in essentially a fixed longitudinal position, so that the entire movement of the movable jaw 18 is laterally displaced with respect to a longitudinal axis of the shaft assembly 14. The very slight lateral movement of the rear pin 54 in the indentation 66 causes a small angular pivoting movement of the pivot link 60 about the pivot pin 62, which results in an extremely slight amount of longitudinal movement of the distal end of the pivot link 60 and the movable jaw 18 as it moves into the intermediate position (FIG. 3) from either the fully open position (FIG. 2) or the fully closed position FIG. 4). However, that extremely slight amount of longitudinal movement is geometrically insignificant or negligible, due to the length of the pivot link 60 and the relatively slight amount of angular pivoting that it experiences.

Figures 6, 7, 8:
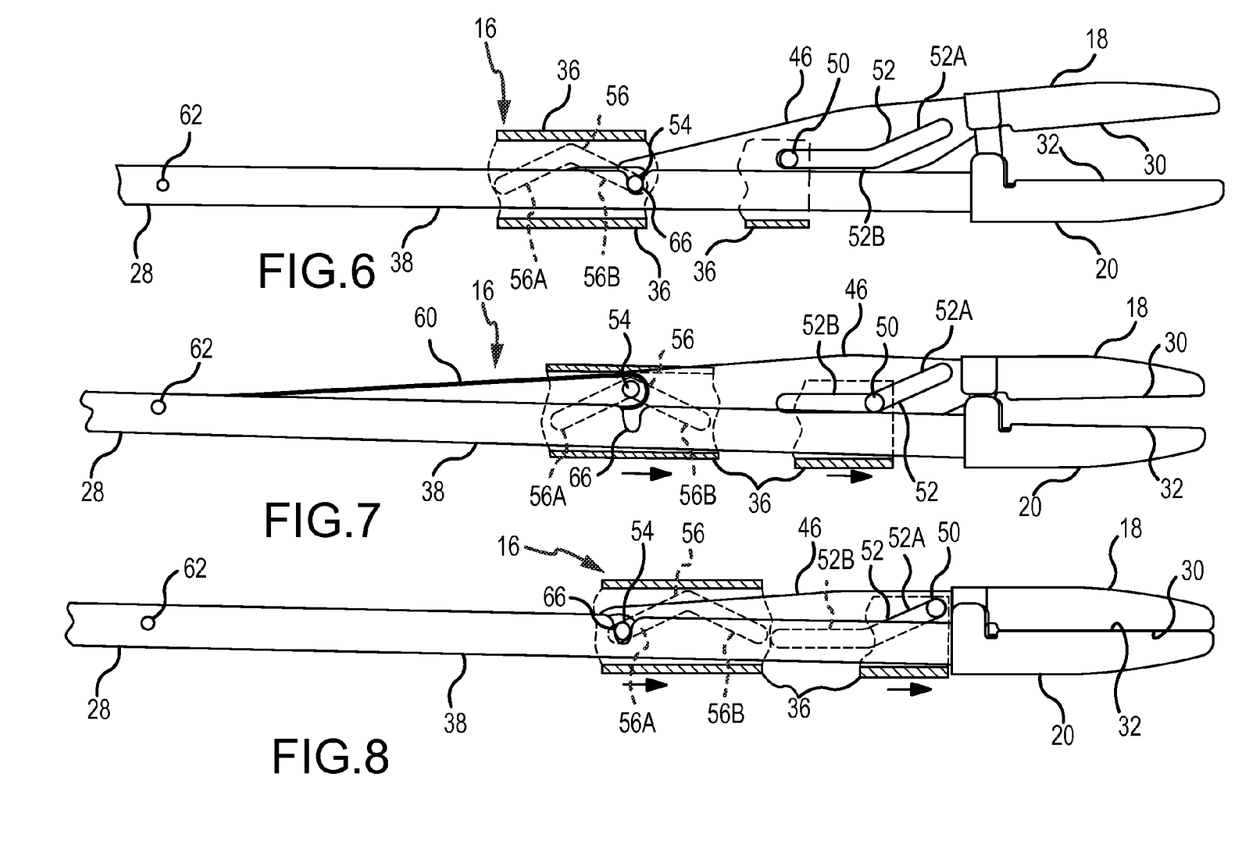
FIGS. 6-8 are side elevational views of certain assembled complete and partial elements of the jaw movement mechanism shown in FIG. 5, with the jaws in the same positions shown in FIGS. 2-4, respectively, and with certain partial portions shown in cross-sectional phantom.

As the sleeve housing 26 reciprocates relative to the interior rod 28, the rear slots 56 move relative to the rear pin 54 and the forward pin 50 moves relative to the forward slot 52. The lateral movement of the extension portion 46 of the movable jaw 18 caused by the relative movement of the pins 50 and 54 in the slots 52 and 56 translates and pivots the movable jaw 18 through the range of motions illustrated by the fully open position (FIGS. 2 and 6), the intermediate position (FIGS. 3 and 7) and the closed position (FIGS. 4 and 8). The movable jaw 18 is prevented from moving any significant longitudinal distance forward or backward relative to the fixed jaw 20 as a result of the pivot link 60. The movable jaw 18 is not otherwise constrained except for the lateral translation and pivoting capability provided by the movement of the pins 50 and 54 in the slots 52 and 56. The angular orientation of the slots 52 and 56 creates and defines the extent of lateral and angular movement of the movable jaw 18 from the amount of relative longitudinal reciprocating motion of the sleeve housing 26 and the interior rod 28.

The shape of the slots 52 and 56 determines the translational position and angular orientation of the moveable jaw 18 relative to the fixed jaw 20. The slots 52 and 56 are both V-shaped, and have slot portions 52A, 56A which intersect with slot portions 52B and 56B at the apexes of the V-shapes, respectively. The slot segments 52A and 56A are parallel to one another in the closed and intermediate positions and extend at an angular orientation to the longitudinal axis of the reciprocating motion of the sleeve housing 26 and the interior rod 28. The slot segments 52B and 56B are angularly oriented with respect to one another. Slot segment 56B is also angularly oriented with respect to the longitudinal axis of the reciprocating motion of the sleeve housing 26 and the interior rod 28, but slot segment 52B is oriented parallel with respect to longitudinal axis of the reciprocating motion of the sleeve housing 26 and the interior rod 28 in the closed and intermediate positions.

When the pins 50 and 54 are positioned within the parallel movement segments 52A and 56A, the jaws 18 and 20 are oriented parallel to one another. The parallel movement range of the jaws 18 and 20 is between the intermediate and closed positions shown in FIGS. 3, 4, 7 and 8. In the intermediate position shown in FIG. 7, the pins 50 and 54 are at the apexes of the V-shaped slots 52 and 56. Further longitudinal forward motion of the sleeve housing 26 relative to the interior rod 28 causes the pins 50 and 54 to move from the apexes along the parallel slot segments 52A and 56A. Movement in this manner continues until the pins 50 and 54 reach the ends of the slot segments 52A and 56A, respectively. As the pins 50 and 54 move from the apexes to the ends of the slot segments 52A and 56A, the working surfaces 30 and 32 move closer to one another as understood by the movement between FIGS. 3 and 4 and FIGS. 7 and 8.

When the pins 50 and 54 are respectively positioned within the angular movement segments 52B and 56B, the jaws 18 and 20 assume an angular orientation with respect to one another. The angular movement range of the jaws 18 and 20 is between the fully open position (FIGS. 2 and 6) and the intermediate position (FIGS. 3 and 7). The degree of angular orientation increases from the intermediate position (FIGS. 3 and 7) to the fully open position (FIGS. 2 and 6) as the sleeve housing 26 moves rearward relative to the interior rod 28. In the intermediate position shown in FIG. 7, the pins 50 and 54 are at the apexes of the V-shaped slots 52 and 56. Further rearward longitudinal reciprocating motion of the sleeve 26 relative to the interior rod 28 causes the pins 50 and 54 to move from the apexes along the angular slot segments 52B and 56B. Movement in this manner continues until the pins 50 and 54 reach the ends of the slot segments 52B and 56B. As the pins 50 and 54 move from the apexes to the ends of the slot segments 52B and 56B, the working surfaces 30 and 32 move further from one another and the working surface 30 becomes angularly oriented with respect to the working surface 32, as understood by the movement between FIGS. 3 and 2 and FIGS. 7 and 6.

The use of the pivot link 60 in the jaw movement mechanism 16 creates a number of significant improvements and advantages over other jaw movement mechanisms typically used in minimally invasive surgical tools. The pivot link 60 maintains the longitudinal position of the movable jaw 18 and thereby allows the movable jaw 18 to both pivot and translate at both pins 50 and 54 into the fully open, intermediate and closed positions. The ability to both laterally translate and pivot one movable jaw 18 at two locations provides a greater range of movement relative to the longitudinal extent of the relative reciprocating movement applied by the handle assembly 12 (FIG. 1).

The pivot link 60 also eliminates a substantial amount of the friction associated with pin and slot guide devices typically used in minimally invasive surgical tools to control the movement of their jaws. Because the pivot link 38 maintains the longitudinal position of the movable jaw 26, it is not necessary for the rear pin 54 or another part of the rear extension portion 46 to be channeled in a vertical slot or guide to maintain the longitudinal position of the movable jaw 26, as is the case in certain previous surgical tools. Maintaining the longitudinal position by contact of the rear pin within a vertical slot or groove, as in certain previous surgical tools, creates friction in the jaw movement mechanism during reciprocating movement of the shaft members, as the rear pin moves within the vertical slot or groove. Additional force is required to overcome this frictional resistance, and the jaw movement mechanism is less effective in converting the mechanical energy delivered through the reciprocating sleeve members into force available to compress tissue between the jaws. In contrast, the pivot link 60 eliminates the friction of the pin moving in the vertical slot to maintain the longitudinal position of the movable jaw 18, and thereby limits the friction losses to that substantially lesser friction occurring between the pins 50 and 54 and the slots 52 and 56, respectively, as the compression of the tissue between the jaws resists the closure of the jaws.

The use of the pivot link 60 thus improves the mechanical efficiency of the jaw movement mechanism 16 over previous jaw movement mechanisms of the type described. As a result of the improved mechanical efficiency, a greater amount of force is translated through the jaw movement mechanism to allow the jaws to more firmly grip the tissue. The improved mechanical efficiency results in less wasted mechanical energy from the handle assembly, and less strenuous squeezing by the surgeon.

In addition to reducing the energy loss due to friction, the configuration of the pins 50 and 54 and slots 52 and 56 achieve increased force over some previous forms of jaw movement mechanisms used in minimally invasive surgical tools. In the jaw movement mechanism 16, compressing the tissue between the intermediate position (FIGS. 3 and 7) and the closed position (FIGS. 4 and 8) involves the slot segment 56A creating upward force on the rear pin 54 of the rear extension portion 46 and the forward pin 50 creating downward force on the slot segment 52A. As the jaws 18 and 20 move closer together, the distance between the pins 50 and 54 increases, as shown in FIGS. 4 and 8. Increasing the distance between the pins 50 and 54 increases the amount of mechanical leverage available compared to the previous distance between the pins 50 and 54, because an increasing distance between the pivot points increases the mechanical advantage or leverage for the same amount of force applied, in accordance with the physics and geometry of a first-class lever. A greater amount of force is therefore available to be applied to the tissue with the jaw movement mechanism 16 of the present invention for an equal amount of applied force.

The greater amount of force available from the jaw movement mechanism 16 is in contrast to the situation in certain previous surgical tools where the pins and slots are mechanically oriented to maintain the distance between the pins. Of course, maintaining the distance between the pins has the effect of not enhancing the amount of mechanical advantage and force available to squeeze or compress the tissue, as is the case of the present invention for a given amount of force. Consequently the surgeon must squeeze the lever of the handle assembly more firmly during tissue compression because no additional mechanical advantage is achieved by maintaining a fixed distance between the pins. Even a small reduction in force required may be significant in easing the strain on the surgeon during the course of a surgical procedure which could last many hours.

These advantages and improvements of the jaw movement mechanism 16 are attained without compromising the known desirable function of evenly compressing the tissue over a range of parallel movement of the working surfaces during tissue sealing procedures, without compromising the other known desirable function of angularly opening the jaws and working surfaces to facilitate grasping the tissue. Compressing tissue evenly is especially important when the surgical tool is used for tissue fusion in which the jaws transmit both the energy for heating the tissue while simultaneously compressing the tissue between the jaws. The even compression of tissue during tissue fusion helps to ensure a leak proof seal of the tissue. Opening the jaws in a parallel orientation after the tissue has been fused reduces the likelihood that the fused tissue will shear and damage the seal. The ability of the jaw movement mechanism to orient the jaws in an angular relationship when the jaws are in the fully opened position allows the jaws to more easily capture tissue between the jaws, which can be particularly important during minimally invasive surgery where monoscopic visualization through the minimally invasive makes depth perception difficult or impossible.

The present invention is adaptable to many types of surgical tools that have jaw movement mechanisms which control the orientation and relative position of a pair of jaws. Such tools may be used for a variety of different surgical procedures such as the grasping tissue or cutting tissue, in addition to sealing tissue. The jaw movement mechanism is also conveniently used with jaws that have working surfaces which transfer thermal heat to the tissue or which function as electrodes to transfer electrical energy through the squeezed tissue. Sometimes, after fusing the tissue, the sealed tissue will be cut. The cutting mechanism is frequently incorporated with the jaws, or the jaws themselves may be used to cut the tissue, such as by applying additional energy after tissue sealing has occurred to cause the tissue to separate.

A presently preferred embodiment of the present invention and many of its improvements have been described with a degree of particularity. This description is of a preferred example of implementing the invention, and is not necessarily intended to limit the scope of the invention. The scope of the invention is defined by the following claims.

What is claimed:

1. A minimally invasive surgical tool having a stationary jaw and a movable jaw for grasping tissue by transverse movement of the moveable jaw relative to the stationary jaw at a distal end of a shaft assembly connected to a handle assembly, the handle assembly creating relative reciprocating movement transferred through a relatively stationary shaft member and a relatively movable shaft member of the shaft assembly to a jaw movement mechanism, the stationary jaw rigidly connected to the relatively stationary shaft member, each jaw has a straight working surface, the working surfaces of the jaws extend at an angular orientation with respect to one another at a fully open position, the working surfaces of the jaws extend at a parallel orientation with respect to one another at an intermediate position, the working surfaces of the jaws extend at a parallel orientation with respect to one another at a fully closed position, the jaw movement mechanism maintains the working surfaces of the jaws in the parallel orientation with respect to one another during transverse movement of the jaws between the intermediate position and the fully closed position, the jaw movement mechanism comprising:
   a pivot link having a proximal end and a distal end, the proximal end of the pivot link pivotally connected to the relatively stationary shaft member by a pivot pin and the distal end of the pivot link pivotally connected to a proximal end of the movable jaw by a rear pin located within a rear slot defining a proximal lateral displacement for each change in longitudinal position of the relatively movable shaft member with respect to the relatively stationary shaft member, the rear slot being formed in the stationary shaft member; and
   a front pin located within a front slot defining a distal lateral displacement for each longitudinal position of the relatively movable shaft member with respect to the relatively stationary shaft member,
   wherein each of the rear slot and the front slot comprises a primary segment defining the respective lateral displacements moving the movable jaw between the intermediate position and the fully closed position, and
   wherein the proximal lateral displacement defined for each longitudinal position in the primary segment of the rear slot is equal to the distal lateral displacement defined for each longitudinal position in the primary segment of the front slot.

2. A minimally invasive surgical tool as defined in claim 1, wherein:
   each of the rear slot and the front slot includes two angularly intersecting portions, a first of the angular intersecting portions being the primary segment and a second of the angular intersecting portions being a secondary segment creating and defining the lateral movement of its respective pin for each longitudinal position therein, the lateral movement of the pins in the secondary segment directly moving the movable jaw between the intermediate position and the fully open position.

3. A minimally invasive surgical tool as defined in claim 2, wherein:
   the primary section of the first slot extends generally parallel to the primary section of the second slot, the primary section of the first and second slots are non-parallel to the direction of relative reciprocating movement of the shaft members.

4. A minimally invasive surgical tool as defined in claim 3, wherein:
   one of the secondary segments of the first and second slots extends at an intersecting angle to the direction of relative reciprocating movement of the shaft members; and
   the other one of the secondary segments of the first and second slots extends at an intersecting angle with respect to said one of the secondary segments of the first and second slots extending at an intersecting angle to the direction of relative reciprocating movement.

5. A minimally invasive surgical tool as defined in claim 2, wherein:
   the first and second pins move respectively in the first and second slots to positions which are farther separated from one another with movement of the jaw members from the intermediate position to the fully closed position.

6. A minimally invasive surgical tool as defined in claim 1, wherein:
   the relatively stationary shaft member comprises an interior rod having an open interior space within which the pivot link moves; and
   the relatively movable shaft member comprises a sleeve housing having an interior which receives the interior rod and within which the pivot link pivots during movement of the jaws between the fully opened and the fully closed positions.

7. A minimally invasive surgical tool as defined in claim 6, wherein:
   the interior of the sleeve housing has a predetermined cross-sectional interior configuration;
   the exterior of the interior rod has a predetermined cross-sectional exterior configuration; and
   the predetermined cross-sectional configurations of the interior and exterior configurations of the sleeve housing and the interior rod permit relative longitudinal reciprocating movement of the sleeve housing and the rod and prevent relative rotational movement of the sleeve housing and the rod.

8. A minimally invasive surgical tool as defined in claim 1, wherein:
   the front slot is defined in the movable jaw and the rear pin is retained by the moveable jaw;
   the front pin is retained by the relatively movable shaft;
   the distance between the first and second pins increases as the jaws are moved from the fully opened position to the fully closed position; and
   the distance between the first and second pins decreases as the jaws are moved from the fully closed position to the fully opened position.

9. A surgical tool as defined in claim 8, wherein:
   the first slot and the second pin are stationary relative to each other; and
   the second slot and the first pin are stationary relative to each other.

10. A minimally invasive surgical tool defined in claim 1, for fusing together tissue compressed between the jaws, wherein the jaws include elements for transferring energy to tissue compressed between the jaws.

* * * * *